(12) United States Patent
Chappuis

(10) Patent No.: US 9,289,242 B2
(45) Date of Patent: Mar. 22, 2016

(54) INTERNAL PEDICLE INSULATOR APPARATUS AND METHOD OF USE

(71) Applicant: James L. Chappuis, Atlanta, GA (US)

(72) Inventor: James L. Chappuis, Atlanta, GA (US)

( * ) Notice: Subject to any disclaimer, the term of this patent is extended or adjusted under 35 U.S.C. 154(b) by 0 days.

(21) Appl. No.: 14/281,013

(22) Filed: May 19, 2014

(65) Prior Publication Data

US 2014/0257391 A1 Sep. 11, 2014

Related U.S. Application Data

(60) Division of application No. 11/712,257, filed on Feb. 28, 2007, now Pat. No. 8,728,132, which is a continuation of application No. 11/110,005, filed on Apr. 20, 2005, now Pat. No. 7,338,500.

(60) Provisional application No. 60/563,797, filed on Apr. 20, 2004.

(51) Int. Cl.
*A61B 17/70* (2006.01)
*A61B 17/68* (2006.01)
*A61F 2/46* (2006.01)

(52) U.S. Cl.
CPC ............ *A61B 17/70* (2013.01); *A61B 17/686* (2013.01); *A61B 17/7098* (2013.01); *A61B 17/7001* (2013.01); *A61F 2002/4631* (2013.01)

(58) Field of Classification Search
CPC combination set(s) only.
See application file for complete search history.

(56) References Cited

U.S. PATENT DOCUMENTS

| | | | |
|---|---|---|---|
| 4,653,489 A * | 3/1987 | Tronzo | 606/65 |
| 4,877,020 A * | 10/1989 | Vich | 606/86 R |
| 4,998,452 A * | 3/1991 | Blum | 81/57.37 |
| 5,562,736 A * | 10/1996 | Ray et al. | 606/86 A |
| 5,609,636 A * | 3/1997 | Kohrs et al. | 623/17.16 |
| 5,782,919 A * | 7/1998 | Zdeblick et al. | 623/17.16 |
| 6,004,326 A * | 12/1999 | Castro et al. | 606/99 |
| 6,048,343 A * | 4/2000 | Mathis et al. | 606/916 |
| 6,086,595 A * | 7/2000 | Yonemura et al. | 606/99 |
| 6,093,207 A | 7/2000 | Pisharodi | |
| 6,139,549 A * | 10/2000 | Keller | 606/86 A |
| 6,214,012 B1* | 4/2001 | Karpman et al. | 606/93 |
| 6,267,763 B1* | 7/2001 | Castro | 606/86 A |
| 6,306,156 B1 | 10/2001 | Clark | |
| 6,387,130 B1* | 5/2002 | Stone et al. | 623/17.16 |
| 6,402,751 B1 | 6/2002 | Hoeck et al. | |
| 6,436,068 B1* | 8/2002 | Bardy | 604/57 |
| 6,436,100 B1* | 8/2002 | Berger | 606/916 |
| 6,827,722 B1* | 12/2004 | Schoenefeld | 606/104 |
| 6,866,664 B2 | 3/2005 | Schar et al. | |
| 7,063,681 B1* | 6/2006 | Peery | 604/60 |
| 7,128,760 B2* | 10/2006 | Michelson | 623/17.15 |
| 7,207,995 B1* | 4/2007 | Vandewalle | 606/104 |
| 7,476,228 B2* | 1/2009 | Abdou | 606/104 |
| 7,569,061 B2* | 8/2009 | Colleran | 606/104 |
| 7,744,632 B2 | 6/2010 | Usher | |
| 7,780,704 B2 | 8/2010 | Markworth et al. | |
| 7,794,478 B2 | 9/2010 | Nilsson | |
| 7,922,747 B2 | 4/2011 | Kirschman | |
| 7,927,355 B2 | 4/2011 | Berrevoets et al. | |
| 7,959,653 B2 | 6/2011 | Thramann et al. | |

(Continued)

*Primary Examiner* — Christian Sevilla

(74) *Attorney, Agent, or Firm* — McHale & Slavin, P.A.

(57) ABSTRACT

Internal pedicle insulator apparatuses and methods are provided. A representative method includes: providing an internal pedicle insulator implant; inserting the implant into a pedicle such that the implant is positioned between a nerve and material that is to be applied in a vicinity of the nerve; applying the material in the vicinity of the nerve; and using the implant to prevent the material from contacting the nerve.

14 Claims, 2 Drawing Sheets

(56) References Cited

U.S. PATENT DOCUMENTS

| | | |
|---|---|---|
| 8,192,467 B2 | 6/2012 | Felix et al. |
| 8,226,688 B2 | 7/2012 | Alain |
| 8,292,924 B2 | 10/2012 | Neary et al. |
| 8,728,132 B2 * | 5/2014 | Chappuis .................... 606/300 |
| 8,900,236 B2 * | 12/2014 | Chappuis ................. 606/86 R |
| 2001/0023355 A1 * | 9/2001 | Danno ......................... 606/188 |
| 2002/0055742 A1 * | 5/2002 | Lieberman ..................... 606/73 |
| 2002/0143401 A1 * | 10/2002 | Michelson ................. 623/17.16 |
| 2002/0188247 A1 * | 12/2002 | Peery ............................. 604/60 |
| 2002/0188301 A1 * | 12/2002 | Dallara et al. ................ 606/104 |
| 2003/0065329 A1 * | 4/2003 | Vaughan ........................ 606/61 |
| 2004/0176765 A1 | 9/2004 | Troxell et al. |
| 2004/0260300 A1 * | 12/2004 | Gorensek et al. .............. 606/86 |
| 2004/0267277 A1 * | 12/2004 | Zannis et al. .................. 606/99 |
| 2005/0055026 A1 | 3/2005 | Biedermann et al. |
| 2005/0071012 A1 * | 3/2005 | Serhan et al. ............. 623/17.16 |
| 2005/0085813 A1 * | 4/2005 | Spitler et al. .................... 606/61 |
| 2005/0090821 A1 | 4/2005 | Berrevoets et al. |
| 2005/0131386 A1 * | 6/2005 | Freeman et al. ............. 604/522 |
| 2005/0228377 A1 | 10/2005 | Chao et al. |
| 2005/0240194 A1 * | 10/2005 | Chappuis ........................ 606/86 |
| 2006/0189999 A1 * | 8/2006 | Zwirkoski ....................... 606/90 |
| 2006/0241658 A1 * | 10/2006 | Cerundolo .................... 606/148 |
| 2006/0271045 A1 | 11/2006 | Hubbard et al. |
| 2006/0271051 A1 | 11/2006 | Berrevoets et al. |
| 2007/0066977 A1 * | 3/2007 | Assell et al. .................... 606/96 |
| 2007/0162027 A1 * | 7/2007 | Chappuis ........................ 606/72 |
| 2007/0173826 A1 * | 7/2007 | Canaveral et al. .............. 606/61 |
| 2007/0219553 A1 * | 9/2007 | Chappuis ........................ 606/61 |
| 2008/0009868 A1 * | 1/2008 | Gotfried et al. ................. 606/63 |
| 2008/0172093 A1 | 7/2008 | Nilsson |
| 2008/0177315 A1 | 7/2008 | Usher |
| 2008/0221623 A1 * | 9/2008 | Gooch .......................... 606/302 |
| 2009/0012623 A1 * | 1/2009 | Sack et al. ................. 623/17.16 |
| 2010/0010545 A1 | 1/2010 | Park et al. |
| 2010/0174320 A1 * | 7/2010 | Truckai et al. ................ 606/279 |
| 2010/0274286 A1 | 10/2010 | Blain et al. |
| 2010/0305612 A1 | 12/2010 | Nilsson |
| 2012/0158060 A1 | 6/2012 | Abrahams et al. |
| 2012/0253397 A1 | 10/2012 | Kraus |
| 2013/0006101 A1 * | 1/2013 | McHugo et al. .............. 600/424 |
| 2014/0257391 A1 * | 9/2014 | Chappuis ...................... 606/246 |

\* cited by examiner (A-A)

(B-B)

INTERNAL PEDICLE INSULATOR APPARATUS AND METHOD OF USE

CROSS-REFERENCE TO RELATED APPLICATIONS

In accordance with 37 C.F.R. 1.76, a claim of priority is included in an Application Data Sheet filed concurrently herewith. Accordingly, the present invention claims priority as a divisional of U.S. patent application Ser. No. 11/712,257, entitled "INTERNAL PEDICLE INSULATOR APPARATUS AND METHOD OF USE", FILED Feb. 28, 2007, which is a continuation-in-part of U.S. patent application Ser. No. 11/110,005, entitled "INTERNAL PEDICLE INSULATOR APPARATUS AND METHOD OF USE", filed Apr. 20, 2005, now U.S. Pat. No. 7,338,500, issued Mar. 4, 2008, which claims priority to U.S. Provisional Patent Application No. 60/563,797, entitled "INTERNAL PEDICLE INSULATOR APPARATUS", filed Apr. 20, 2004, the contents of the above-referenced applications are incorporated herein by reference in their entirety.

FIELD OF THE INVENTION

The present invention generally relates to surgical instruments and tools, and in particular, relates to an internal pedicle insulator apparatus.

BACKGROUND OF THE INVENTION

The human spine is composed of a column of thirty-three bones, called vertebra, and their adjoining structures. The twenty-four vertebrae nearest the head are separate bones capable of individual movement and are generally connected by anterior and posterior longitudinal ligaments and by discs of fibrocartilage, called intervertebral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of the vertebra include a vertebral body and a dorsal arch, which enclose an opening, called the vertebral foramen, through which the spinal cord and the spinal nerve pass. The remaining nine vertebrae below the lumbar spine are fused to form the sacrum and the coccyx and are incapable of individual movement.

Degeneration of the lumbar spine can be cause the human spine is composed of a column of thirty-three bones, called vertebra, and their adjoining structures. The twenty-four vertebrae nearest the head are separate bones capable of individual movement and are generally connected by anterior and posterior longitudinal ligaments and by discs of fibrocartilage, called intervertebral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of the vertebra include a vertebral body and a dorsal arch, which enclose an opening, called the vertebral foramen, through which the spinal cord and the spinal nerve pass. The remaining nine vertebrae below the lumbar spine are fused to form the sacrum and the coccyx and are incapable of individual movement.

The degeneration of any portion of the lumbar spine can result in instability of the spine, which can lead to impingement or damage to the spinal cord or nerve roots. Impingement of the spinal column or nerve root can result in pain. Damage to spinal cord or nerve roots can result in reduced motor skills or even paralysis. Degeneration of the lumbar spine can be a result of fractures, tumors or other various degenerative diseases.

It is well known that utilization of pedicle screws for posterior lumbar stabilization procedures. These procedures typically include inserting a pedicle screw posteriorly into the pedicle or pillar of the lumbar spine. The screw is then connected to plates or rods for stabilization of the lumbar spine. A bone graft also can be added to help solidify the stabilization. The pedicle screw may be inserted off center, such as, for example, too medial, which may impinge on the associated nerve root causing pain. This requires a repositioning of the screw. However, even after repositioning there may be an effect on the pedicle wall, which can still cause nerve root irritation. Such procedures are also susceptible to loosening of the screw.

Thus, a heretofore unaddressed need exists in the industry to address the aforementioned deficiencies and inadequacies.

SUMMARY OF THE INVENTION

Internal pedicle insulator apparatuses and methods are provided. An exemplary embodiment of such a method comprises: providing an internal pedicle insulator implant; inserting the implant into a pedicle such that the implant is positioned between a nerve and material that is to be applied in a vicinity of the nerve; applying the material in the vicinity of the nerve; and using the implant to prevent the material from contacting the nerve.

An exemplary embodiment of an internal pedicle insulator apparatus, comprises: an inner insertion rod having a top end and an opposing bottom end; an outer insertion rod having an upper end and a lower end, the outer insertion rod being arranged and configured to substantially correspond to the inner insertion rod; and an internal pedicle insulator implant. The inner insertion rod is arranged and configured to be slidably engaged inside the outer insertion rod, and the inner insertion rod and the outer insertion rod are arranged and configured to position the internal pedicle insulator implant such that material applied in a vicinity of a nerve located in a pedicle is prevented from irritating the nerve by being mechanically blocked by the internal pedicle insulator implant.

Another exemplary embodiment of an internal pedicle insulator apparatus, comprises: an inner insertion rod having a top end and an opposing bottom end; an outer insertion rod having an upper end and an opposing lower end; and an internal pedicle insulator implant. The inner insertion rod and the outer insertion rod are arranged and configured to insert and position the internal pedicle insulator implant such that cement used to secure a pedicle screw does not irritate a nerve located in a vicinity of the cement.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Figure 1:
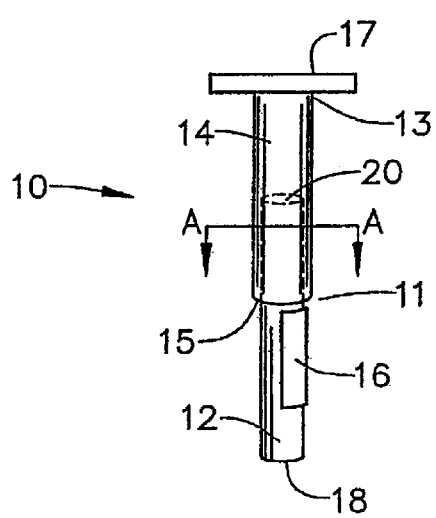
FIG. 1 is a side view of an embodiment of the internal pedicle insulator apparatus of the present invention.

FIG. 1 illustrates one preferred embodiment of an internal pedicle insulator apparatus 10. The internal pedicle insulator apparatus 10 comprises an inner insertion rod 12, an outer insertion rod 14, and an internal pedicle insulator implant 16.

The inner insertion rod 12 has a bottom end 18 and an opposing top end 20. It is preferable that the inner insertion rod 12 has a substantially round cross-section. However, it should be noted that the inner insertion rod 12 can comprise any suitable configuration. The inner insertion rod 12 can comprise any suitable material, such as titanium, as merely one example.

The outer insertion rod 14 has a lower end 11 and an opposing upper end 13. An opening 15 is disposed at the lower end 11. An optional handle 17 can be disposed toward the upper end 13 of the outer insertion rod 14 to facilitate use of the internal pedicle insulator apparatus 10. An opening at the upper end 13 of the outer insertion rod 14 through which the inner insertion rod 12 can pass can also be included (not shown). It is preferable that the outer insertion rod 14 has a substantially round cross-section. It should be noted, however, that the outer insertion rod 14 can comprise any suitable cross-section. The outer insertion rod 14 can comprise titanium, however, it should be understood that the outer insertion rod 14 can comprise any suitable material.

The outer insertion rod 14 is arranged and configured to receive the inner insertion rod 12 through the opening 15 disposed at the lower end 11 of the outer insertion rod 14. The inner insertion rod 12 is preferably slidably inserted into the outer insertion rod 14 such that the upper end 13 of the outer insertion rod 12 substantially corresponds to the top end 20 of the inner insertion rod 12. Similarly, the lower end 11 of the outer insertion rod 14 substantially corresponds with the bottom end 18 of the inner insertion rod 12. The inner insertion rod 12 is laterally slidable within the outer insertion rod 14.

Figure 1A:
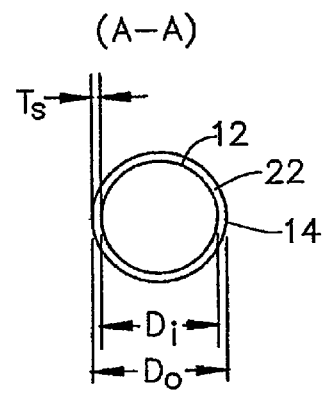
FIG. 1A is a cross-sectional top view of an embodiment of the internal pedicle insulator apparatus illustrated in FIG. 1.

Referring next to FIG. 1A, in one embodiment it is preferable that the outer insertion rod 14 is defined by a diameter $D_o$. The inner insertion rod 12 is defined by a diameter $D_i$. It is preferable that $D0$ is greater than $D_i$ to facilitate the inner insertion rod 12 being slidably disposed within the outer insertion rod 14. It is further preferable that $D_o$, is less than $D_i$ such as to leave a space 22 having a thickness $T_s$ when the inner insertion rod 16 is disposed within the outer insertion rod 14.

Figure 1B:
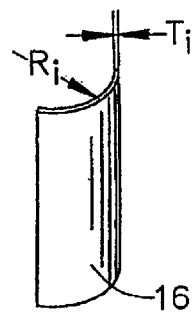
FIG. 1B is a perspective view of an embodiment of an internal pedicle insulator implant of the internal pedicle insulator apparatus illustrated in FIG. 1.

As shown in FIG. 1B, in one embodiment the internal pedicle insulator implant 16 is substantially rectangular in shape and curved. It should be understood, however, that the internal pedicle insulator implant 16 can comprise any suitable shape and configuration. In this embodiment it is preferable that the internal pedicle insulator implant 16 is curved as defined by a radius $R_i$. It is preferable that the radius $R_i$ of the internal pedicle insulator implant 16 substantially corresponds to a pedicle screw 104 with which the internal pedicle insulator implant 16 is to be used. The internal pedicle insulator implant 16 is also defined by a thickness $T_i$. It is preferable that the thickness $T_i$ is greater than the thickness $T_s$ of space 22. The internal pedicle insulator implant 16 preferably comprises Poly Ether Ether-Ketone, but can comprise any suitable material.

Figure 2:
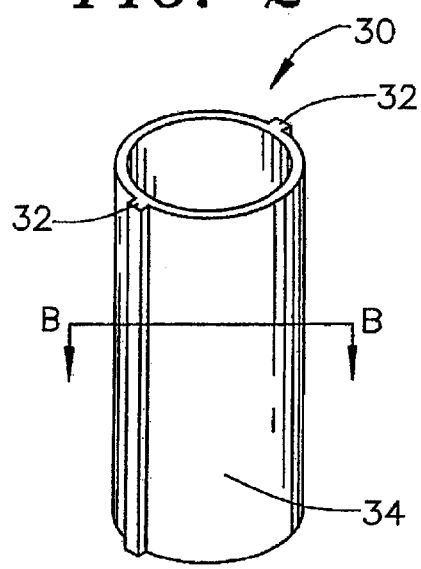
FIG. 2 is a perspective view of an embodiment of an internal pedicle insulator implant of the internal pedicle insulator apparatus illustrated in FIG. 1.
Figure 2A:
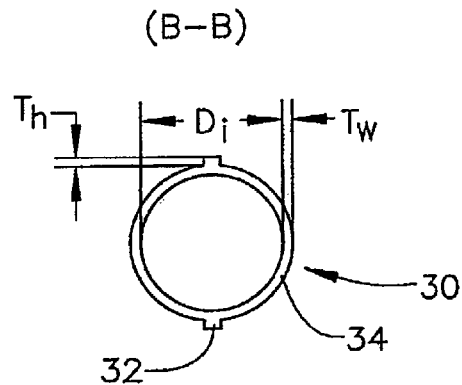
FIG. 2A is a cross-sectional top view of an embodiment of an internal pedicle insulator implant illustrated in FIG. 2.

FIGS. 2 and 2A illustrate another embodiment of an internal pedicle insulator implant 30. The internal pedicle insulator implant 30 is substantially tubular in shape and comprises a wall 34. The internal pedicle insulator implant 30 has a substantially circular cross-section, defined by a diameter $D_i$. The diameter $D_i$ is preferably arranged and configured to substantially correspond to a pedicle screw 104 with which the internal pedicle insulator implant 30 is to be used. Although a substantially circular cross-section is illustrated, it should be understood that the internal pedicle insulator can have any desired cross-sectional shape.

The internal pedicle insulator 30 optionally comprises at least one anti-rotation fin 32 extending outward from the wall 34. The anti-rotation fins 32 can extend the length of the wall 34 of internal pedicle insulator 30 or only a portion of the length. The anti-rotation fins 32 can comprise any configuration that discourage rotation of the internal pedicle insulator 30 when disposed in a desired position. In one embodiment, a thickness $T_w$ of the wall 34 of the internal pedicle insulator implant 30 in addition to a height $T_h$ of an anti-rotation fin 32 extending from the wall 34 is greater than thickness $T_s$ of the space 22 between the inner insertion rod 12 and the outer rotation rod 14 when the inner insertion rod 12 is disposed within the outer rotation rod 14.

In another embodiment the internal pedicle insulator implant 30 includes no anti-rotation fin 32 (not shown). In this embodiment, it is preferable that a thickness $T_w$ of a wall of the internal pedicle insulator implant 30 is greater than the thickness $T_s$ of the space 22 formed by the inner insertion rod 12 and the outer insertion rod 14 when the inner insertion rod 12 is disposed inside the outer insertion rod 14.

Figure 3:
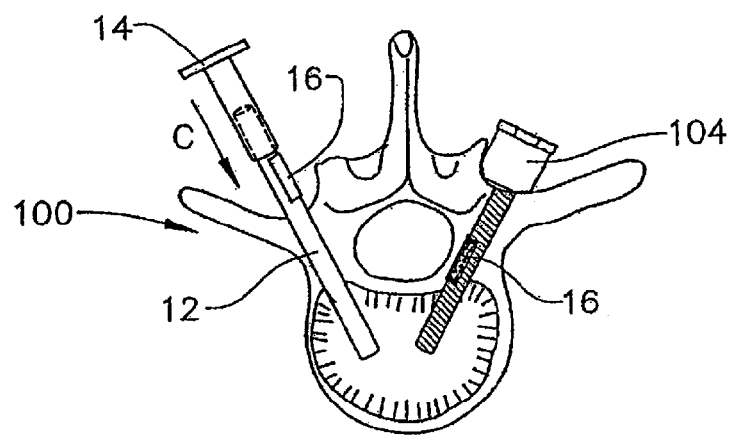
FIG. 3 is a side view of the internal pedicle insulator apparatus illustrated in FIG. 1 in use.

FIG. 3 illustrates the internal pedicle insulator apparatus 10 in use. A pedicle screw with which the internal pedicle insulator implant 16 is to be used is first removed from its position within the vertebral body. The inner insertion rod 12 is positioned as desired in the vertebral body 100, such as in a channel created by the pedicle screw 104. The internal pedicle insulator implant 16 is positioned adjacent the inner insertion rod 12. The outer insertion rod 14 is positioned around the inner insertion rod 12 via the opening 15 disposed at the lower end 11 of the outer insertion rod 14. The outer insertion rod 14 is moved in direction C toward the bottom end 18 of the inner insertion rod 12. As the outer insertion rod 14 is moved in direction C, the outer insertion rod 14 is moved toward the internal pedicle insulator implant 16 until the outer insertion rod 14 engages the internal pedicle insulator 16. Pressure is applied to the outer insertion rod 14 in direction C to slide the internal pedicle insulator 16 along the inner insertion rod 12 toward the vertebral body 100 until the internal pedicle insulator 16 is appropriately positioned within the vertebral body 100. The internal pedicle insulator implant is held in position by friction applied to its curved configuration when properly inserted into position. After the internal pedicle insulator implant 16 is disposed in a desired position, the pedicle screw 104 is returned to its position within the vertebral body.

Figure 4:
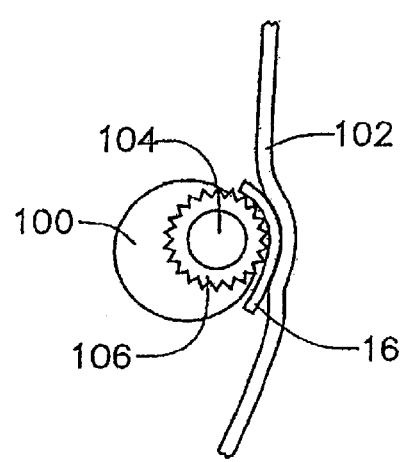
FIG. 4 is a top view of the internal pedicle insulator implant of the internal pedicle insulator apparatus illustrated in FIG. 1 in use.

FIG. 4 illustrates one embodiment of an internal pedicle insulator implant 16 in a desired position. As shown, the internal pedicle insulator implant 16 is positioned between an affected nerve root 102 and a jagged hole 106 in the vertebral body 100 resulting from a compromised pedicle screw 104.

Figure 5:
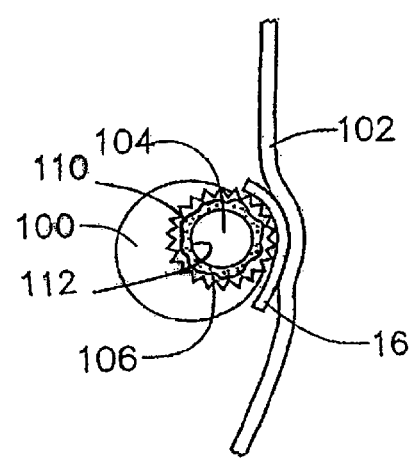
FIG. 5 is a top view of another embodiment of an internal pedicle insulator implant of the internal pedicle insulator apparatus in use.

FIG. 5 illustrates another embodiment of an internal pedicle insulator implant 16. In this example, however, the implant is located to prevent cement, e.g., PMMA, from contacting the nerve root 102. Notably, the cement 110 is provided to anchor the pedicle screw 104. In other embodiments, various other types of materials can be prevented from contacting a nerve by using an implant. Such a material can be an injectable biological substance, for example.

Although cement can be provided externally with respect to the screw, the embodiment of FIG. 5 involves a screw that incorporates holes or fenestrations e.g., fenestration 112. As such, the cement can be injected into the screw and then a portion of that cement can be pass through the fenestrations and into the surrounding tissue. Thus, the implant 16 serves as a physical barrier to prevent the cement from impinging upon the nerve root.

It should be emphasized that the above-described embodiments of the present invention, particularly, a "preferred" embodiment, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein with the scope of this disclosure and the present invention and protected by the following claims.

What is claimed is:

1. An internal pedicle insulator apparatus, comprising:
an inner insertion rod having a top end and an opposing bottom end; and
an outer insertion rod having an upper end and a lower end, the outer insertion rod being arranged and configured to substantially correspond to the inner insertion rod; and
an internal pedicle insulator implant having a thickness greater than a thickness of a space separating said inner and said outer insertion rod when said inner insertion rod is disposed within said outer insertion rod;
wherein the inner insertion rod is arranged and configured to slidably engaged inside the outer insertion rod, and the inner insertion rod and the outer insertion rod are arranged and configured to position the internal pedicle insulator implant such that material applied in a vicinity of a nerve located in a pedicle is prevented from irritating the nerve by being mechanically blocked by the internal pedicle insulator implant.

2. The internal pedicle insulator apparatus of claim 1, wherein the inner insertion rod is slidably disposed concentrically within the outer insertion rod.

3. The internal pedicle insulator apparatus of claim 1, wherein the inner insertion rod is substantially tubular in shape and the outer insertion rod is substantially tubular in shape.

4. The internal pedicle insulator apparatus of claim 1, further comprising: a handle disposed toward the upper end of the outer insertion rod and extending therefrom.

5. The internal pedicle insulator apparatus of claim 1, wherein the material is cement used to anchor a pedicle screw in the pedicle.

6. The internal pedicle insulator apparatus of claim 5, wherein the internal pedicle insulator implant comprises a substantially rectangular configured material being curved.

7. The internal pedicle insulator apparatus of claim 5, wherein the internal pedicle insulator implant comprises a substantially tubular configured material defined by a wall.

8. The internal pedicle insulator apparatus of claim 7, wherein the internal pedicle insulator implant further comprises an anti-rotation fin extending from the wall.

9. An internal pedicle insulator apparatus, comprising:
an inner insertion rod having a top end and an opposing bottom end;
an outer insertion rod having an upper end and an opposing lower end; and
an internal pedicle insulator implant having a thickness greater than a thickness of a space separating said inner and said outer insertion rod when said inner insertion rod is disposed within said outer insertion rod;
wherein the inner insertion rod and the outer insertion rod are arranged and configured to insert and position the internal pedicle insulator implant such that cement used to secure a pedicle screw does not irritate a nerve located in a vicinity of the cement.

10. The internal pedicle insulator apparatus of claim 9, wherein the inner insertion rod is slidably engaged concentrically inside the outer insertion rod.

11. The internal pedicle insulator apparatus of claim 9, wherein the internal pedicle insulator implant comprises a substantially rectangular configured material being curved.

12. The internal pedicle insulator apparatus of claim 9, wherein the internal pedicle insulator implant comprises a substantially tubular configured material defined by a wall.

13. The internal pedicle insulator apparatus of claim 12, wherein the internal pedicle insulator implant further comprises an anti-rotation fin extending from the wall.

14. The internal pedicle insulator apparatus of claim 9, further comprising:
a handle disposed toward the upper end of the outer insertion rod and extending therefrom.

* * * * *